United States Patent

Kagermeier

[11] Patent Number: 6,078,947
[45] Date of Patent: *Jun. 20, 2000

[54] MEDICAL INSTALLATION SYSTEM

[75] Inventor: Robert Kagermeier, Nuremberg, Germany

[73] Assignee: Siemens Aktiengesellschaft, Munich, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/919,809

[22] Filed: Aug. 29, 1997

[30] Foreign Application Priority Data

Aug. 30, 1996 [DE] Germany .......................... 196 35 233

[51] Int. Cl.[7] ...................... G06F 15/163; A61B 5/0205
[52] U.S. Cl. .............................. 709/203; 709/3; 709/102; 709/203; 378/115; 364/121; 364/267; 600/483
[58] Field of Search ...................... 395/183.07, 183.08, 395/183.22, 184.04, 185.01, 680, 672; 707/201; 714/46; 709/3, 102, 203; 378/115; 600/483; 364/121, 267

[56] References Cited

U.S. PATENT DOCUMENTS

| | | | |
|---|---|---|---|
| 5,179,702 | 1/1993 | Spix et al. | 395/672 |
| 5,388,252 | 2/1995 | Dreste et al. | 395/183.22 |
| 5,400,792 | 3/1995 | Hoebel et al. | 600/483 |
| 5,692,129 | 11/1997 | Sonderegger et al. | 709/203 |

OTHER PUBLICATIONS

IEEE Computer, 1984, pp. 73–83 entitled: "An Autonomous, Decentralized Control System for Factory Automation".

Primary Examiner—Zarni Maung
Assistant Examiner—Hieu C. Le
Attorney, Agent, or Firm—Hill & Simpson

[57] ABSTRACT

A medical installation system including at least one medical therapy and/or diagnostics apparatus having a controller with a control computer, and further including at least one computer work station connected to a first data network. The control computer is connected thereto via a second data network separated from the first data network such that the computer work station and the control computer are capable of communicating with one another.

21 Claims, 2 Drawing Sheets

MEDICAL INSTALLATION SYSTEM

BACKGROUND OF THE INVENTION

1. Field of the Invention

The invention is directed to a medical installation system including at least one medical therapy and/or diagnostics apparatus having a controller containing a control computer, at least one computer work station and a data network to which both the control computer and the computer work station are connected such that the computer work station may communicate with the control computer.

2. Description of the Prior Art

The aforementioned type of medical installation system is employed, for example, in clinics wherein therapy and/or diagnostics apparatus are connected to computer work stations via a data network. For report preparation and other similar tasks, therefore, one has the option to load data from the medical therapy and/or diagnostics apparatus into a computer work station via the data network.

A potential problem with such systems, however, is that, due to disturbances or misuse, the therapy and/or diagnostics apparatus might be activated separate and apart from the computer work station connected to the associated data network, thereby allowing the data stored in the therapy and/or diagnostics apparatus to be modified. This unfortunately might lead to inconsistent data and, accordingly, medically disadvantageous consequences for a patient.

SUMMARY OF THE INVENTION

The present invention is based on the object of fashioning a medical installation system of the type initially cited wherein the risk of an improper communication between a computer work station and a therapy and/or diagnostics apparatus connected to the same data network is at least reduced.

This object is achieved by a medical installation system including at least one medical therapy and/or diagnostics apparatus having a controller containing a control computer, at least one computer work station, a first data network and a second date network. The system is configured such that the control computer is connected to the computer work station via the second data network which is separated from the first data network. The computer work station is, however, also separately connected to the first data network.

The possibility of improper access into the medical therapy and/or diagnostics apparatus is significantly reduced due to the employment of two separate data networks. Indeed, inadmissible access from a computer work station other than one connected to the therapy and/or diagnostics apparatus via the first data network presumes an unauthorized penetration into the second data network.

Injuries to patients may be precluded when, according to an embodiment of the present invention, the computer work station is connected to the control computer via the second data network such that the computer work station and the control computer are only capable of communicating with one another when a data transmission occurs from the control computer to the computer work station; an influencing of the medical therapy and/or diagnostics apparatus in communication with the computer work station then being impossible. Such configuration does not represent any limitation for a user making proper use of the computer work station since the operation of the therapy and/or diagnostics apparatus in communication with the computer work station is not provided anyway.

According to an embodiment of the present invention, the computer work station contains two network interfaces wherein one serves for the connection to the first data network and the other serves for the connection to the second data network. As a result, a hardware separation of the two data networks is assured and enhanced security is realized.

In the interest of lower costs, a preferred embodiment of the invention provides that the control computer be a commercially-available personal computer and/or that the computer work station contains a commercially-available personal computer. It is particularly advantageous in this context when the computers work with an operating system having integrated network functionality. Such functionality serves for the realization of the second data network so that no additional software outlay need be expended. Rather, only a slight re-configuration of the software is necessary.

Additional features and advantages of the present invention are described in, and will be apparent from, the detailed description of the presently preferred embodiments and from the drawings.

DETAILED DESCRIPTION OF THE PREFERRED EMBODIMENTS

Figure 1:
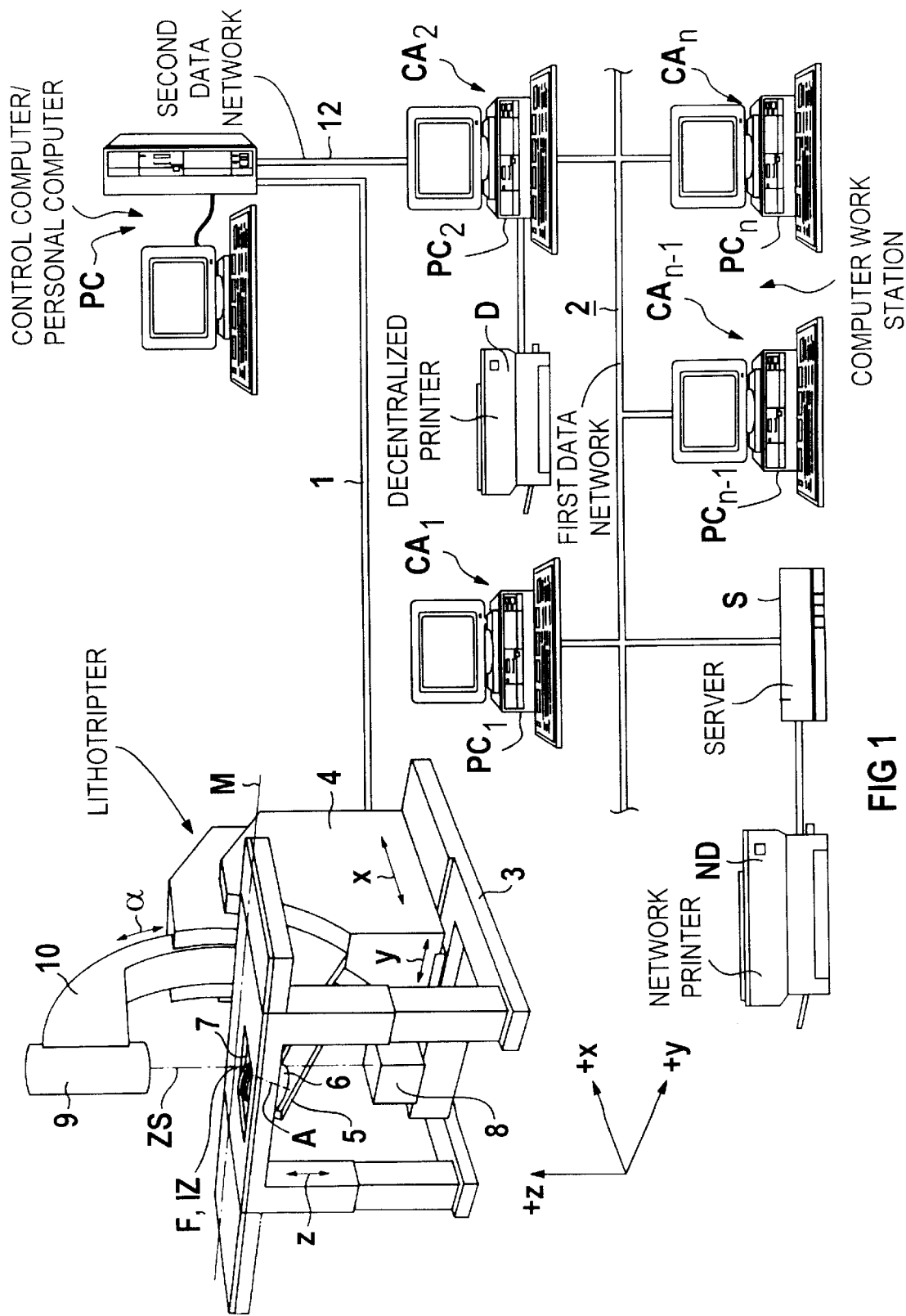
FIG. 1 shows a perspective view of a lithotripter connected to a schematically-indicated data network in accordance with the principles of the present invention.

FIG. 1 shows a medical therapy and diagnostics apparatus, namely a lithotripter, whose control is maintained by a commercially-available personal computer PC. Such a control computer and associated operating control is disclosed, for example, in German Patent No. DE 43 41 290 A1. To this end, the lithotripter includes an interface (not shown in FIG. 1) by which it is connected to the personal computer PC with a line 1. The personal computer PC comprises a system unit with bulk storage (a hard disk, for example), a keyboard and a monitor.

FIG. 1 also shows a first data network that contains a plurality of n computer work stations, of which only four are shown; namely, the computer work stations $CA_1$, $CA_2$, $CA_{n-1}$ and $CA_n$. Also shown are a server S and a network printer ND that are connected to one another via a network line 2. Each of the computer work stations contains a commercially-available personal computer PC in the described exemplary embodiment which comprises a system unit with bulk storage a keyboard and a monitor. These personal computers are indicated by the reference characters $PC_1$ through $PC_n$.

The lithotripter includes a patient bearing table 3 upon which a subject may be treated. The bearing plate of the table is height-adjustable via two telescoping columns in the direction of the double arrow z with reference to a pedestal 4. A carrier part 5 is adjustable on the pedestal 4 in the direction of the double arrow y and in the direction of the double arrow x with a carriage arrangement. The directions of the double arrows x, y and z correspond to the axes of a rectangular spatial coordinate system referenced in FIG. 1. With a holder 6, a source 7 of focussed acoustic waves is attached to the carrier part 5. Such source 7 may be, for example, an electromagnetic pressure pulse source of the type disclosed in European Patent No. EP-A-0 372 110.

The source 7 includes an acoustic axis A on which the focus zone F of the acoustic pressure pulses generated by the source 7 lies. The source 7 has a flexible bellows-like coupling pillow which projects through an opening of the bearing plate of the patient bearing table 3. The coupling pillow assumes a position in which the focus zone F is located in an isocenter IZ above the bearing surface of the bearing plate.

An X-ray diagnostics apparatus is also attached to the carrier part 5 which includes, among other things, an X-radiator 8 and an X-ray image intensifier lying opposite thereto. These elements are attached to the ends of an arcuately-shaped C-bend 10. The C-bend 10 is attached to the carrier part 5 and is relatively adjustable thereto along its circumference in the direction of the curved double arrow α such that it can be swivelled around its middle axis M. The central ray ZS of the X-ray diagnostics apparatus intersects the middle axis M of the C-bend 10 at a right angle. The arrangement disclosed ensures that the middle axis M and the central ray ZS proceed through the isocenter IZ and, thus, through the focus F.

The adjustment of the bearing plate of the patient bearing table 3 in the z-direction and of the X-ray diagnostics apparatus in the x, y, and α-directions occurs by motor, preferably electromotively. For treating a patient, the patient is first placed on the bearing plate of the patient bearing table 3 such that the body region to be treated (for example, a kidney stone contained in a kidney), is located above the opening of the bearing plate. With the assistance of the X-ray diagnostics apparatus, the carrier part 5 is adjusted in the x and in y directions and the bearing plate of the patient bearing table 3 is adjusted in the x-direction so that the region to be treated is located in the isocenter IZ and, thus, in the focus zone F. To that end, it is necessary to transirradiate the patient with the X-ray diagnostics apparatus from various directions by adjusting the C-bend 10 in the α-direction.

When the region to be treated is situated in the focus zone F, the source 7 which is acoustically coupled to the body surface of the patient with the flexible coupling pillow is activated and, given repeated monitoring with the X-ray diagnostics apparatus, the region to be treated is charged with pressure pulses until the desired outcome of the treatment has been achieved. Using the kidney stone example, such desired outcome occurs when the kidney stone has been disintegrated into such small fragments that they can be eliminated in a natural way.

The specific data which corresponds to every treatment (for example, a patient's name, date of birth, etc., the number and intensity of the applied pressure pulses as well as the X-ray images prepared before and after the treatment), is stored in a specific directory on the hard disk of the personal computer PC functioning as the operating facility and control computer. This data, which might include ANSI and/or ASCII text datafiles as well as graphics datafiles, for example in PCX format, are referred to below as treatment data. In order to access the treatment data stored in the personal computer PC serving as the operating facility and control computer in the first data network, both the personal computer PC and one of the computer work stations of the first data network—the computer work station $CA_2$ in the illustrated exemplary embodiment—are combined via a network line 12 to form a second data network separated from the first.

Figure 2:
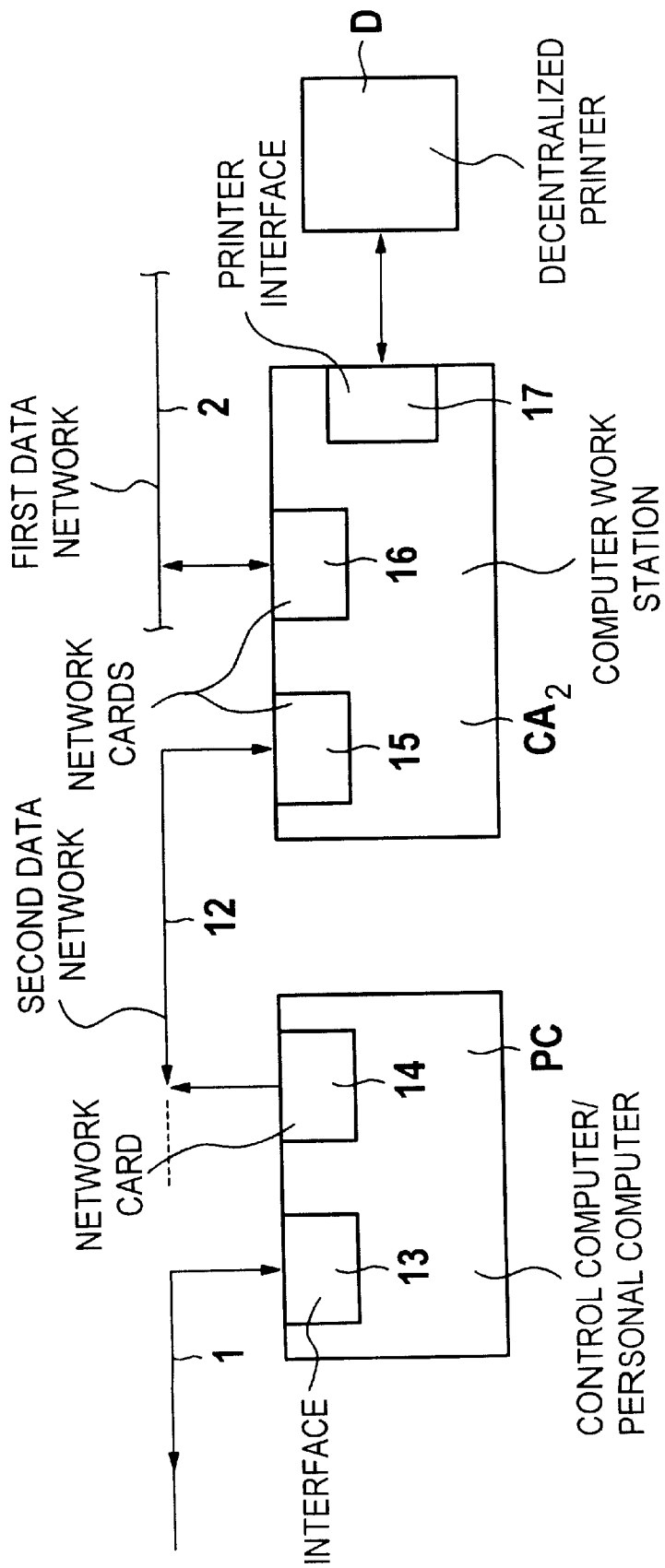
FIG. 2 shows a block circuit diagram of the lithotripter connected to the data network from FIG. 1.

Referring now to the block diagram of FIG. 2, the personal computer PC serving as the operating facility and control computer contains an interface 13 which allows it to communicate, via the line 1, with the aforementioned lithotripter having a corresponding interface. In addition, the personal computer PC contains a network card, for example, an Ethernet card 14, by which it can communicate over the network line 12 with the computer work station $CA_2$ in the framework of the second data network. The computer work station $CA_2$ likewise has an Ethernet card 15 serving for the realization of the second data network available to it. A thin coaxial cable with a characteristic impedance of 50 Ohms (what is referred to as a Thin Ethernet) is provided as network line 12 which can have a length of up to 30 m. As indicated by a broken-line extension of the network line 12 in FIG. 2, there is the possibility of involving one or more further computer work stations in the second data network.

Both the personal computer PC serving as the operating facility and control computer and the computer work station $CA_2$ (as well as further devices potentially connected to the second data network) work with the same operating system, for example Windows for Workgroups 3.11®. Such an operating system already contains a network function by which the communication can be sequenced in the second data network; for example, according to the network protocol NETBUI, a Microsoft® standard. In the described exemplary embodiment, the network function is configured such that only read accesses onto the password-protected directory specifically provided for storing the treatment data can be carried out from the computer work station $CA_2$. Moreover, the network function is configured such that accesses, particularly write accesses, onto other directories of the hard disk of the personal computer PC are fundamentally impossible. This concept is illustrated in FIG. 2 wherein an arrow proceeds only from the Ethernet card 14 of the personal computer PC serving as the operating facility and control computer to the network line 12 and from the latter to the Ethernet card 15 of the computer work station $CA_2$.

To ensure the connection of the computer work station $CA_2$ to the first data network, the computer work station $CA_2$ contains a second network card 16; for example, another Ethernet card. The first data network is implemented in an arbitrary technology, preferably differing from that of the second data network, such as a Novell network. Read and write accesses are thereby made possible between the computer work stations $CA_1$ through $CA_n$, as indicated by a double arrow between the Ethernet card 16 and the network line 2, only a portion of the latter being shown in FIG. 2.

If so desired, it is possible to configure the network function of the first data network such that treatment data can also be accessed from other computer work stations, but only such data located in the computer work station $CA_2$ and not in the personal computer PC. There is, accordingly, also the possibility of restricting the access possibilities to the data stored in the computer work station $CA_2$ in that, for example, access is only allowed onto specific directories of the hard disk of the computer work station $CA_2$.

There is further the possibility of configuring the network function of the first data network such that the printing of treatment data out on the network printer ND is allowed. If it is undesirable to transmit treatment data via the first data network, yet desirable to have printing capabilities, a decentralized printer D must be connected to the computer work station $CA_2$ connected via the second data network employing a suitable printer interface 17, as shown in FIGS. 1 and 2.

If there should only be the possibility within the first data network of viewing treatment data, it suffices that the computer work stations provided with a corresponding authorization have corresponding text and/or image viewing software available to them. Insofar as the possibility of processing the treatment data should also be established, computer work stations provided with a corresponding authorization must also contain a suitable text editor or text processing program; for example, Microsoft WinWord® and/or a suitable, commercially available image processing program. The software outlay to be expended in conjunction with the viewing and/or processing of the treatment data within the first data network is thus so slight that the software used can be standard products, insofar as suitable data formats are selected for the treatment data.

The operating system used within the second data network can be, but need not be, identical to the operating system used within the first data network. When Windows for Workgroups 3.11® is employed as the operating system within the second data network, then, for example, Windows for Workgroups 3.11®, Windows 95® or Windows NT® (version 3.51 or 4.0) are suitable, for example, as operating systems for the first data network. Further, it is also possible that a German-language operating system version can be employed within the first data network and an English-language operating system can be employed in the second data network.

Although the present invention has been described with reference to a specific embodiment, those of skill in the art will recognize that changes may be made thereto without departing from the spirit and scope of the invention as set forth in the hereafter appended claims.

I claim as my invention:

1. A medical installation system, comprising:
   a first data network;
   a second data network separated from the first data network;
   at least one medical apparatus having a control computer connected to the second data network, wherein the control computer provides exclusive computer control of the medical apparatus; and
   at least one computer work station connected to both the first data network and the second data network, wherein the second data network provides for only uni-directional data transmission from the control computer to the computer work station, and wherein the first data network provides for bidirectional data transmission only between the computer work station and additional computer work stations, if present, and not to the control computer.

2. The medical installation system as claimed in claim 1, further comprising:
   first and second network interfaces in the computer work station, the first network interface serving for the connection to the first data network and the second network interface serving for the connection to the second data network.

3. The medical installation system as claimed in claim 1, further comprising:
   first and second network interfaces in the computer work station, the first network interface serving for the connection to the first data network and the second network interface serving for the connection to the second data network.

4. The medical installation system as claimed in claim 1, further comprising:
   a commercially-available personal computer as part of the control computer.

5. The medical installation system as claimed in claim 1, further comprising:
   a commercially-available personal computer as part of the computer work station.

6. The medical installation system as claimed in claim 1, further comprising:
   a commercially-available personal computer as part of the control computer.

7. The medical installation system as claimed in claim 1, further comprising:
   a commercially-available personal computer as part of the computer work station.

8. A medical installation system as claimed in claim 2, further comprising:
   a commercially-available personal computer as part of the control computer.

9. The medical installation system as claimed in claim 2, further comprising:
   a commercially-available personal computer as part of the computer work station.

10. The medical installation system as claimed in claim 4, further comprising:
    an operating system with integrated network function as part of the personal computer, the operating system serving for the operation of the second data network.

11. The medical installation system as claimed in claim 5, further comprising:
    an operating system with integrated network function as part of the personal computer, the operating system serving for the operation of the second data network.

12. The medical installation system as claimed in claim 6, further comprising:
    an operating system with integrated network function as part of the personal computer, the operating system serving for the operation of the second data network.

13. The medical installation system as claimed in claim 7, further comprising:
    an operating system with integrated network function as part of the personal computer, the operating system serving for the operation of the second data network.

14. The medical installation system as claimed in claim 8, further comprising:
    an operating system with integrated network function as part of the personal computer, the operating system serving for the operation of the second data network.

15. The medical installation system as claimed in claim 9, further comprising:
    an operating system with integrated network function as part of the personal computer, the operating system serving for the operation of the second data network.

16. The medical installation system as claimed in claim 1, further comprising:
    a printer as part of the computer work station.

17. The medical installation system as claimed in claim 1, further comprising:
    a printer as part of the computer work station.

18. The medical installation system as claimed in claim 2, further comprising:
    a printer as part of the computer work station.

19. The medical installation system as claimed in claim 3, further comprising:
    a printer as part of the computer work station.

20. The medical installation system as claimed in claim 1, wherein the medical apparatus is a medical therapy device.

21. The medical installation system as claimed in claim 1, wherein the medical apparatus is a diagnostics device.

* * * * *